United States Patent
Musani

(10) Patent No.: US 8,961,490 B2
(45) Date of Patent: Feb. 24, 2015

(54) DISPOSABLE VIAL HOLDER AND METHOD TO PREVENT NEEDLE STICK INJURIES

(75) Inventor: Ali I. Musani, Centennial, CO (US)

(73) Assignee: National Jewish Health, Denver, CO (US)

( * ) Notice: Subject to any disclaimer, the term of this patent is extended or adjusted under 35 U.S.C. 154(b) by 79 days.

(21) Appl. No.: 12/879,258

(22) Filed: Sep. 10, 2010

(65) Prior Publication Data

US 2012/0065611 A1    Mar. 15, 2012

(51) Int. Cl.
| | | |
|---|---|---|
| *A61B 19/02* | (2006.01) | |
| *A61M 5/178* | (2006.01) | |
| *A61M 5/32* | (2006.01) | |
| *A61B 17/34* | (2006.01) | |
| *G21F 5/018* | (2006.01) | |
| *A61B 5/15* | (2006.01) | |
| *A61B 19/00* | (2006.01) | |

(52) U.S. Cl.
CPC .............. *A61M 5/1782* (2013.01); *G21F 5/018* (2013.01); *A61M 5/321* (2013.01); *A61B 5/1405* (2013.01); *A61M 5/3205* (2013.01); *A61B 19/0288* (2013.01); *A61M 5/3202* (2013.01); *A61B 17/3494* (2013.01); *A61B 19/0287* (2013.01); *A61M 5/3213* (2013.01); *A61M 5/1785* (2013.01); *A61B 17/3496* (2013.01); *A61B 2019/4805* (2013.01)
USPC ............ 604/415; 604/187; 604/192; 604/263

(58) Field of Classification Search
CPC . A61M 5/3202; A61M 5/3205; A61M 5/321; A61M 5/3213; A61M 2005/3215; A61M 2005/3213; A61M 5/008; A61M 5/3204; A61M 5/1782; A61M 5/1785; B01L 9/06; A61B 2019/4805; A61B 19/0287; A61B 19/0288; A61B 19/30; A61B 2019/30; A61B 5/14; A61B 5/1405; A61B 5/1444; A61B 17/3494; A61B 17/3496; B65D 85/78; A23G 9/50; A23G 9/503; A23G 9/506; F21V 35/00; F21V 35/006; G21F 5/018
USPC .................... 604/164.08, 187, 192, 197, 263
See application file for complete search history.

(56) References Cited

U.S. PATENT DOCUMENTS

| | | | | |
|---|---|---|---|---|
| 4,559,042 A | * | 12/1985 | Votel .............................. | 604/192 |
| 4,573,975 A | * | 3/1986 | Frist et al. ..................... | 604/192 |
| 4,629,453 A | * | 12/1986 | Cooper ......................... | 604/192 |
| 4,737,149 A | * | 4/1988 | Gillilan ......................... | 604/192 |
| 4,742,910 A | * | 5/1988 | Staebler ........................ | 206/365 |

(Continued)

OTHER PUBLICATIONS

Dictionary entry for "unitary" from http://dictionary.reference.com/browse/unitary?r=66. Accessed Jan. 27, 2014.*

(Continued)

*Primary Examiner* — Adam Marcetich
(74) *Attorney, Agent, or Firm* — Sheridan Ross P.C.

(57) ABSTRACT

A vial holder is provided to protect a user's hand from needle sticks. The holder includes a handle and a shield attached to a distal end of the handle. An opening is formed in the distal end of the handle to receive a vial. The vial is placed through the opening and into a passageway of the handle with the upper end of the vial exposed. A user grasps the handle which holds the vial in a stabilized manner. A needle may then safely approach the vial in which inadvertent slippage or movement of the needle results in contact with the needle against the shield and not contact with the user's hand.

16 Claims, 4 Drawing Sheets

(56) References Cited

U.S. PATENT DOCUMENTS

| | | | |
|---|---|---|---|
| 4,840,618 A | 6/1989 | Marvel | |
| 4,900,309 A * | 2/1990 | Netherton et al. | 336/192 |
| 4,955,865 A | 9/1990 | Steiner et al. | |
| 4,986,817 A * | 1/1991 | Code | 604/192 |
| 5,037,400 A * | 8/1991 | Curry | 604/192 |
| 5,067,944 A * | 11/1991 | Nichols | 604/192 |
| 5,078,696 A * | 1/1992 | Nedbaluk | 604/192 |
| 5,190,532 A * | 3/1993 | Yu | 604/192 |
| 5,330,439 A | 7/1994 | Jackson | |
| 5,451,213 A * | 9/1995 | Teicher et al. | 604/192 |
| 5,505,705 A * | 4/1996 | Galpin et al. | 604/192 |
| 5,624,404 A | 4/1997 | Fisler | |
| 5,951,524 A * | 9/1999 | Enriquez | 604/192 |
| 6,375,027 B1 * | 4/2002 | Thomas et al. | 220/23.83 |
| 6,464,105 B1 | 10/2002 | Rolle et al. | |
| 6,648,857 B1 | 11/2003 | Pedigo | |
| 6,684,406 B2 | 2/2004 | Fowler | |
| D507,833 S | 7/2005 | Coss | |
| 2006/0108319 A1 | 5/2006 | Meittunen | |
| 2007/0054019 A1 * | 3/2007 | Sotile | 426/420 |
| 2007/0148296 A1 * | 6/2007 | Price et al. | 426/420 |
| 2008/0167622 A1 * | 7/2008 | Noppen | 604/192 |

OTHER PUBLICATIONS

Dictionary entry for "unitary" from http://www.thefreedictionary.com/unitary. Accessed Jan. 27, 2014.*

International Search Report for International (PCT) Patent Application No. PCT/US11/48915, mailed Dec. 15, 2011.

Written Opinion for International (PCT) Patent Application No. PCT/US11/48915, mailed Dec. 15, 2011.

International Preliminary Report on Patentability for International (PCT) Patent Application No. PCT/US11/48915, mailed Mar. 21, 2013, 6 pages.

* cited by examiner

DISPOSABLE VIAL HOLDER AND METHOD TO PREVENT NEEDLE STICK INJURIES

FIELD OF THE INVENTION

The invention relates to devices and methods to prevent needle stick injuries, and more particularly, to a vial or ampule holder incorporating a protective shield to prevent needle stick injuries.

BACKGROUND OF THE INVENTION

Medical personnel are required to constantly handle needles used for various purposes to include intravenous injections or shots. In order to administer the shots, the syringe must be filled with the substance to be injected. The user is required to manipulate the needle to draw the substance typically from a small vial or ampule. The ampule usually has a rubber cork that is pierced by the tip of the needle in order to draw its contents. Often, because of the sterile nature of the procedures, the ampule or vial is held by a nurse or a technician while the physician inserts the needle in the vial/ampule. This process is frequently repeated during a single procedure. Less commonly, the vial/ampule is held in one hand and needle in the other hand of the same person. Because of the difficulty in handling the vial/ampule in both methods and along with the number of times in which medical personnel must administer injections, it is inevitable that medical personnel will receive needle stick injuries. Contaminated needles from patients can and have infected health care providers with potentially lethal infections such as Hepatitis and HIV/AIDS.

Contact of the needle with a person contaminates the needle requiring disposal of the syringe that may have already withdrawn some of the material from the vial/ampule.

There are number of prior art devices that have been developed over time to prevent needle stick injuries. One example of a prior art device includes a hand guard device as disclosed in U.S. Pat. No. 6,684,406. Another type of protective device includes a syringe holder as disclosed in U.S. Pat. No. 6,464,105. Yet another example of a prior art device includes a vial attachment to prevent needles sticks as disclosed in the U.S. Patent Publication No. 2006/0108319. This publication more particularly discloses a protective disc that attaches to the neck of the vial/ampule. The protective disc has a circular orifice that enables the attachment of the disc to the vial yet allows access to the pierceable membrane/seal of the ampule. Yet another example of a prior art device to prevent needle stick injuries is shown in the U.S. Pat. No. 6,648,857. This reference discloses a protective shield that receives a spent needle.

While the prior art may be adequate for its intended purpose, there is still a need for a device to prevent needle stick injuries that is easy to use, relatively inexpensive, easy to manufacture, and can be made sterile for use in an operating room environment. There is yet a further need to provide such a device that not only shields the user's hand, but also enhances the user's ability to hold the vial/ampule of different sizes thereby further preventing potential needle sticks which may occur by the inability to adequately grasp the vial/ampule.

SUMMARY OF THE INVENTION

The present invention provides a disposable vial holder and method to prevent needle stick injuries. The disposable vial holder includes a handle that is grasped by the user, and a shield that overlies the handle to protect the user's hand. A distal end of the handle includes a vial opening to receive the vial/ampule. The vial opening may be slightly tapered in order to accommodate different sizes of vials. The user secures the vial and inserts it within the vial opening in which the upper end of the vial is exposed. The user then grasps the handle, and the needle may then safely approach the vial for withdrawing the contents of the vial.

Preferably, the shield is circular shaped which provides a configuration for covering the hand. Alternatively, the shield may have one side thereof which is extended to further cover the hand and part of the user's wrist. The vial holder to include the shield is preferably made from a needle impenetrable material, such as an adequate selection of a plastic material. Additionally, the vial holder can be transparent, sterile, disposable, and recyclable. The handle can be made of a softer material as compared to the shield which may provide the user with a better grip for holding the vial.

In one preferred embodiment, the shield is substantially planer and extends substantially perpendicular to an axis of the handle. In yet another embodiment, the axis of the handle may extend at an angle other than perpendicular from the shield to better facilitate access to the ampule by the person manipulating the needle.

According to the method of the invention, the vial holder is secured by the user and a vial is placed within the vial opening. The user grasps the handle such that the hand is effectively covered by the shield. The user or another person may then manipulate the needle of a syringe to withdraw the contents of the vial into the syringe. The needle is separated from the vial. The vial and vial holder may then be disposed of together, or the vial holder and vial may be separated from one another and then disposed of separately.

Other features and advantages of the invention will become apparent from a review of the following detailed description taken in conjunction with the drawings.

BRIEF DESCRIPTION OF THE DRAWINGS

FIGS. 1-4 illustrate the vial or ampule holder 10 in two preferred embodiments. The vial holder has two primary components, namely, a shield 12 and a handle 14. The handle 14 as shown is substantially cylindrical. Alternatively, the handle can have a multi-faceted surface, such as may be provided with the handle having a heptagonal or octagonal shaped cross section (not shown). The handle 14 is hollow along a portion of its length as defined by a vial opening 16 that communicates with an internal passageway 18. Preferably the passageway 18 is tapered in order to receive different sized vials. The shield 12 as shown has a substantially circular shape, but the shape of the shield may be modified to ensure coverage of the user's hand. The shape of the shield 12 may be extended to also cover a portion of the user's hand near the wrist, as explained below in reference to FIG. 6.

As shown in FIG. 2 in an alternative embodiment, a protruding flange 30 is illustrated that may further assist in stabilizing and holding the vial. As shown, the depth of the passageway 18 is the same as FIG. 2, but the protruding flange 30 provides additional coverage for holding the side surface of the vial.

Referring to FIGS. 3 and 4, the depth of the passageway 18 may be adapted to accommodate the appropriate sized vials V such that the lower end of the vial V is seated against the bottom of the passageway. As shown, the remaining portion of the handle may be solid which enhances stability for holding by the user. Alternatively, the passageway can be sized and tapered to only frictionally hold the sidewall of the vial V and therefore have depth greater than the length of the vial.

Referring to FIG. 5, in use, a vial V is inserted within the opening 16, and the passageway 18 covers the vial V with exception of the upper end of the vial that may protrude beyond the shield 12. This configuration enables a secure connection for holding the vial, yet enables easy access to the vial by the needle of a syringe. Because the vial is held within the holder, this provides additional stability for the user to prevent inadvertent slippage or movement of the needle as it penetrates the seal of the vial. The user's hand H is protected by the shield, and the diameter of the shield ensures that most or all of the exposed edge of the hand cannot be contacted by the needle N of the syringe S.

Figure 1:
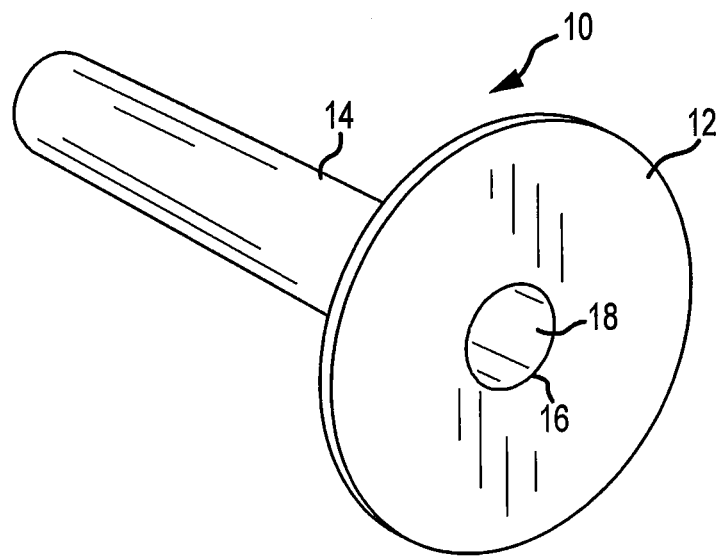
FIG. 1 is perspective view of a first preferred embodiment.
Figure 2:
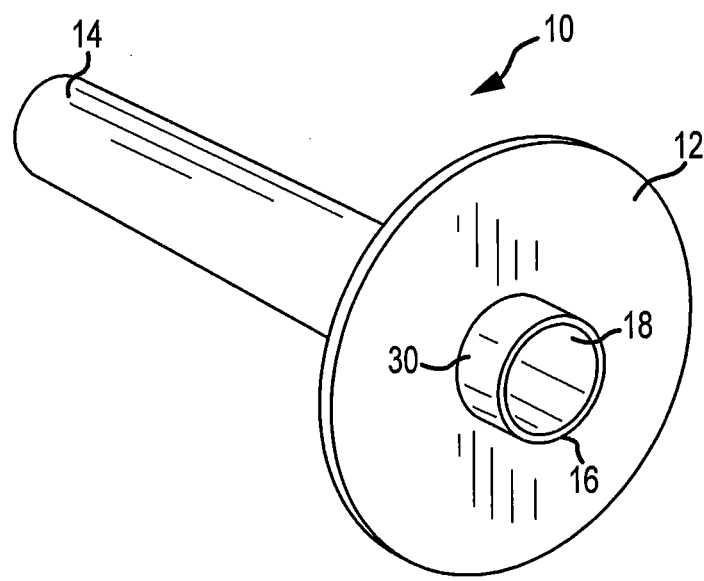
FIG. 2 is a perspective view of a second preferred embodiment.
Figure 3:
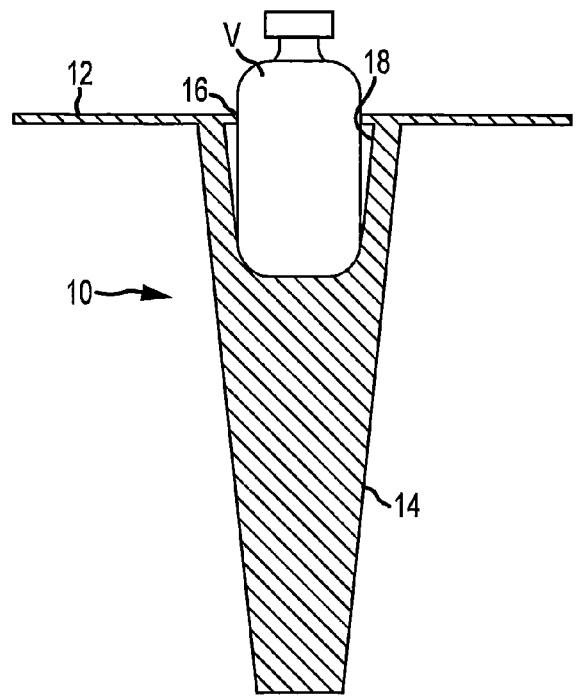
FIG. 3 is a cross-sectional view of FIG. 1 showing the holder securing an ampule.
Figure 4:
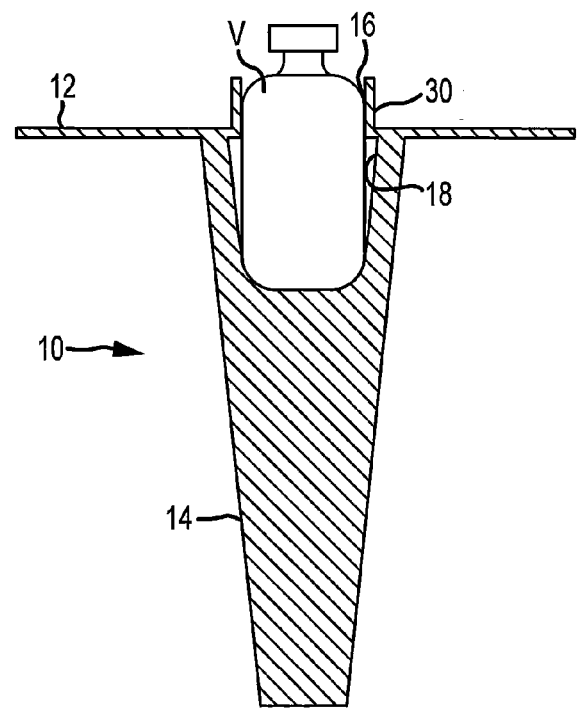
FIG. 4 is a cross-sectional view of FIG. 2 showing the holder securing an ampule.

Optionally, the shield may be made of a bright color which may further assist the person in manipulating the syringe to direct the needle toward the vial and to ensure the needle is appropriately centered to penetrate the seal of the vial. Otherwise, the vial holder itself may be made of clear plastic material or any other color. As shown in the preferred embodiment of FIGS. 3 and 4, the vial holder is made as a single unitary member.

Figure 6:
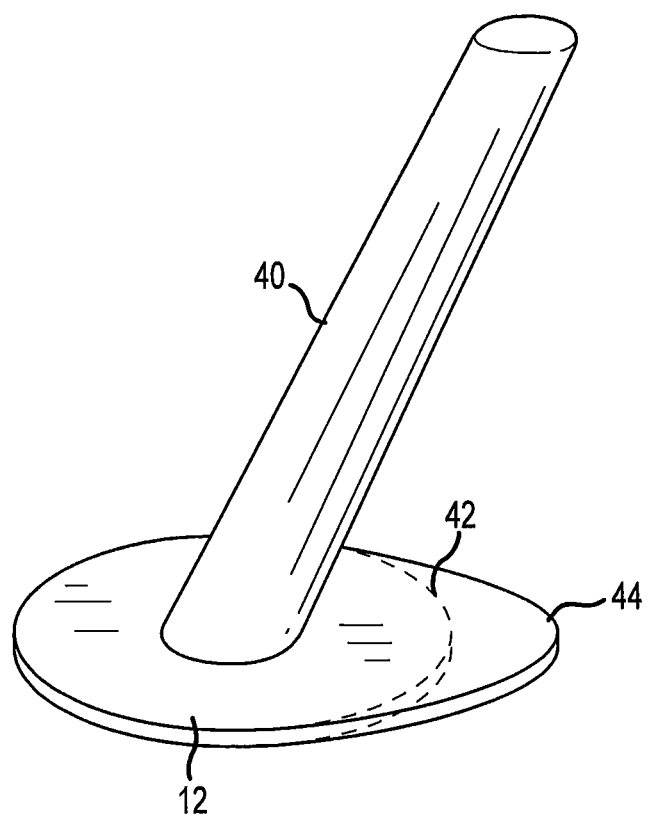
FIG. 6 is a perspective view of yet another preferred embodiment in which the handle is angled from the shield.

Referring to FIG. 6, an alternative embodiment is illustrated in which the handle 40 does not extend substantially perpendicular to the plane of the shield 12, but rather, extends at an angle. Therefore, it is contemplated that the handle itself may be manufactured with a slight offset as compared to only a perpendicular arrangement between the handle and shield. This angle or offset handle may be advantageous to better align the user's hand with the approaching needle, and may depend on the preference of the user as to either an angled or perpendicular arranged handle. FIG. 6 also illustrates the shield 12 having an extension 44 located along a portion of the peripheral edge of the shield 12. An imaginary line 42 is shown as the circular diameter in which the size and shape of the extension 44 can be compared. The extension can be centered over the user's wrist to provide an additional area of protection.

Figure 5:
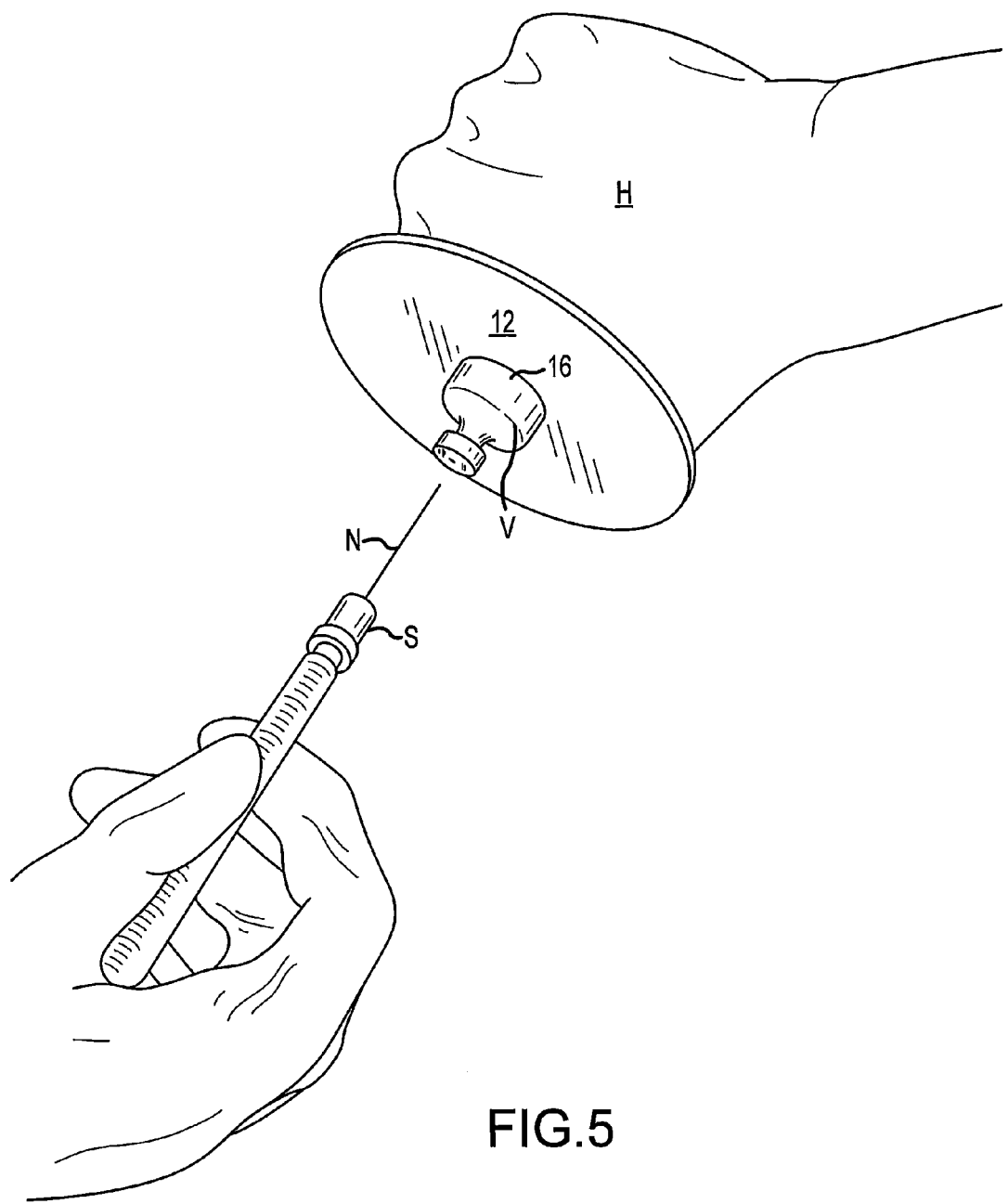
FIG. 5 is a perspective view showing use of the first embodiment in which a user holds the holder in the hand, while another person holds a syringe in preparation for contacting the needle of the syringe with the ampule.

Although the FIG. 5 illustrates the user grasping the handle in a particular manner, the invention is not limited to any particular manner of grasping by the user and accordingly, the user may wish to most comfortably position the fingers around the handle. For example, the user could simply hold the handle with the fingers in which the proximal end of the handle is placed in the palm of the user's hand. Further, while the shield has been illustrated as having a particular size and shape, the present invention also contemplates varying the size and shape of the shield to correspond with the method of use in which the positioning of the user's hand may dictate the area of the shield in order to cover the portions of the hand that may be exposed to a needle stick.

According to a particular method of the present invention, the vial holder V is provided and a user secures a vial within the passageway 18. The tapered passageway enables the user to seat the vial within the passageway with a desired frictional resistance in which the vial does not seat in the bottom of the passageway but rather is held by the sidewalls of the passageway. Once the vial has been secured, a user grasps the handle 14 and the needle may then be safely moved towards the vial. Once the needle has withdrawn the contents of the vial, the needle is separated from the vial and the vial holder and vial may be disposed of. Alternatively, prior to disposal, the vial holder and vial may be separated from one another.

The vial holder and method of the present invention provides a convenient, reliable, and cost-effective way in which to prevent needle stick injuries. The unique combination of the handle and shield not only provides protection for the user, but also enhances the stability of the vial to prevent slippage of the needle when making contact with the vial. The invention is easily incorporated into surgical room procedures in which the vial holder can be made sterile and disposable. Many different types of plastics can be used for the vial holder, to include a wide selection for desired colors, stiffness, and imperviousness to needle penetrations.

While the present invention has been set forth with respect to one or more preferred embodiments it is contemplated that various other changes and modifications may be made to the invention commensurate with the scope of the claims appended hereto.

The invention claimed is:

1. A vial holder comprising:
   a handle having an opening formed at distal end thereof, and a passageway communicating with said opening, said passageway extending a depth within a portion of the handle from said distal end toward a proximal end of said handle;
   a substantially planar shield attached to a distal end of the handle, the shield extending substantially perpendicular to an axis of the handle, and the shield having a shape to cover a user's hand that grasps the handle;
   a flange connected to and protruding from said opening, and said flange extending radially inward into said passageway;
   said passageway is continuosly tapered commencing at a larger diameter at said opening to a smaller diameter towards said proximal end of said handle; and
   wherein said vial holder is made as a single member.

2. A holder, as claimed in claim 1, wherein:
   said handle extends substantially perpendicular to the plane of the shield.

3. A holder, as claimed in claim 1, wherein:
   said shield is made from a needle impenetrable plastic having a first stiffness, and said handle is made from a plastic having a second lesser stiffness.

4. A holder, as claimed in claim 1, wherein:
   said shield is substantially circular shaped.

5. A holder, as claimed in claim 1, wherein:
   said shield is a curve shaped with an extension formed on one side of the shield.

6. A holder, as claimed in claim 1, wherein:
   said handle includes a smaller proximal end and a larger distal end.

7. A holder, as claimed in claim 1, wherein:
   said flange is substantially co-planar with said shield.

8. A holder, as claimed in claim 1, wherein:
   said passageway is smooth.

9. A vial holder comprising:
   a handle having an opening formed at distal end thereof, and a passageway communicating with said opening, said passageway extending a depth within a portion of the handle from said distal end toward a proximal end of said handle, and said passageway is continuously tapered commencing at a larger diameter at said opening to a smaller diameter towards said proximal end;

a substantially planar shield attached to a distal end of the handle, and said shield having a shape to cover a user's hand that grasps the handle;

wherein said vial holder is made as a single member; and a flange communicating with said shield and having a proximal end extending from said opening away from said handle, and said flange having a distal end extending away from said opening.

10. A method of preventing needle stick injuries during use of a needle in withdrawing contents of a vial, said method comprising:

providing a vial holder including a handle having a passageway extending partially through said handle, said handle having a proximal and distal end;

providing a substantially planar shield attached to a distal end of the handle, the shield extending substantially perpendicular to an axis of the handle, and the shield having a shape to substantially cover an edge of user's hand grasping the handle;

providing a vial with contents therein, and frictionally holding the vial within the passageway of the vial holder, said vial having a base and a cylindrical sidewall extending from said base, wherein a lower portion of said cylindrical sidewall contacts an interior surface of said passageway, and an upper portion of said cylindrical sidewall located within said passageway is spaced from and not in contact with said interior surface of said passageway;

grasping and holding the handle of the vial holder;

moving a needle toward the upper end of the vial;

withdrawing contents within vial; and wherein said passageway is continuously tapered commencing at a larger diameter at said opening to a smaller diameter towards said proximal end of said handle.

11. In combination, a vial holder and vial comprising:

a handle having a passageway extending a depth within a portion of the handle;

a substantially planar shield attached to a distal end of the handle, and the shield having a shape to cover a user's hand that grasps the handle;

said passageway extends from an opening formed in the distal end of said handle to a depth within the handle and toward said proximal end of said handle, said passageway having an interior surface, and continuously tapered commencing at a larger diameter at said opening to a smaller diameter towards said proximal end of said handle; and a vial with contents therein secured in said passageway of said vial holder, said vial having an upper end that remains exposed and not placed within the passageway, said vial having a base and a cylindrical sidewall extending from said base, wherein a lower portion of said cylindrical sidewall contacts said interior surface of said passageway, and an upper portion of said cylindrical sidewall located within said passageway is spaced from and not in contact with said smooth surface of said passageway.

12. A combination, as claimed in claim 11, further including:

a flange connected to and protruding from said opening, and said flange extending radially inward into said passageway.

13. A combination, as claimed in claim 12, wherein:

said flange is substantially co-planar with said shield.

14. A combination, as claimed in claim 11, wherein:

said handle includes a smaller proximal end and a larger distal end.

15. A combination, as claimed in claim 11, wherein:

said passageway is smooth.

16. A combination, as claimed in claim 11, wherein:

said shield extends substantially perpendicular to an axis of the handle.

* * * * *

UNITED STATES PATENT AND TRADEMARK OFFICE
CERTIFICATE OF CORRECTION

| | | |
|---|---|---|
| PATENT NO. | : 8,961,490 B2 | Page 1 of 1 |
| APPLICATION NO. | : 12/879258 | |
| DATED | : February 24, 2015 | |
| INVENTOR(S) | : Ali I. Musani | |

It is certified that error appears in the above-identified patent and that said Letters Patent is hereby corrected as shown below:

In the Claims

Column 4, line 39, claim 1,
Following "said passageway is": DELETE "continuosly" and INSERT --continuously--.

Signed and Sealed this
Ninth Day of June, 2015

Michelle K. Lee
*Director of the United States Patent and Trademark Office*